(12) United States Patent
Bortner

(10) Patent No.: US 9,404,155 B2
(45) Date of Patent: Aug. 2, 2016

(54) ALTERNATIVE NUCLEIC ACID SEQUENCING METHODS

(71) Applicant: APPLIED BIOSYSTEMS LLC, Carlsbad, CA (US)

(72) Inventor: Scott Bortner, Palo Alto, CA (US)

(73) Assignee: Applied Biosystems, LLC, Carlsbad, CA (US)

(*) Notice: Subject to any disclaimer, the term of this patent is extended or adjusted under 35 U.S.C. 154(b) by 483 days.

(21) Appl. No.: 13/860,769

(22) Filed: Apr. 11, 2013

(65) Prior Publication Data

US 2013/0303381 A1    Nov. 14, 2013

Related U.S. Application Data

(63) Continuation of application No. 12/200,595, filed on Aug. 28, 2008, now abandoned.

(60) Provisional application No. 60/968,834, filed on Aug. 29, 2007.

(51) Int. Cl.
    *C40B 20/08*      (2006.01)
    *C12Q 1/68*      (2006.01)
    *G06F 19/22*      (2011.01)

(52) U.S. Cl.
    CPC ............ *C12Q 1/6874* (2013.01); *C12Q 1/6869* (2013.01); *G06F 19/22* (2013.01); *C40B 20/08* (2013.01)

(58) Field of Classification Search
None
See application file for complete search history.

(56) References Cited

U.S. PATENT DOCUMENTS

| | | |
|---|---|---|
| 5,305,509 A | 4/1994 | Yuhara et al. |
| 5,616,478 A | 4/1997 | Chetverin et al. |
| 5,641,658 A | 6/1997 | Adams et al. |
| 5,750,341 A | 5/1998 | Macevicz |
| 5,763,594 A | 6/1998 | Hiatt et al. |
| 5,808,045 A | 9/1998 | Hiatt et al. |
| 5,872,244 A | 2/1999 | Hiatt et al. |
| 5,958,698 A | 9/1999 | Chetverin et al. |
| 5,990,300 A | 11/1999 | Hiatt et al. |
| 6,001,568 A | 12/1999 | Chetverin et al. |
| 6,060,288 A | 5/2000 | Adams et al. |
| 6,090,592 A | 7/2000 | Adams et al. |
| 6,210,891 B1 | 4/2001 | Nyren et al. |
| 6,232,465 B1 | 5/2001 | Hiatt et al. |
| 6,255,475 B1 | 7/2001 | Kwiatkowski |
| 6,258,568 B1 | 7/2001 | Nyren |

(Continued)

FOREIGN PATENT DOCUMENTS

| | | |
|---|---|---|
| WO | 93/05183 | 3/1993 |
| WO | 00/18957 | 4/2000 |

(Continued)

OTHER PUBLICATIONS

PCT/US08/74678, International Search Report mailed Nov. 18, 2008.

(Continued)

*Primary Examiner* — Christian Boesen

(57) ABSTRACT

Embodiments are provided that provide for parallel sequencing of nucleic acid segments. In some embodiments, a single sequence is sequenced by at least two different sequencing techniques and the results compared, allowing for deficiencies or strengths of one technique to be complemented by the second technique.

9 Claims, 3 Drawing Sheets

(56) References Cited

U.S. PATENT DOCUMENTS

| | | |
|---|---|---|
| 6,306,597 B1 | 10/2001 | Macevicz |
| 6,309,836 B1 | 10/2001 | Kwiatkowski |
| 6,406,848 B1 | 6/2002 | Bridgham et al. |
| 6,511,803 B1 | 1/2003 | Church et al. |
| 6,613,513 B1 | 9/2003 | Parce et al. |
| 6,613,523 B2 | 9/2003 | Fischer et al. |
| 6,654,505 B2 | 11/2003 | Bridgham et al. |
| 6,664,079 B2 | 12/2003 | Ju et al. |
| 6,806,052 B2 | 10/2004 | Bridgham et al. |
| 6,806,058 B2 | 10/2004 | Jesperson et al. |
| 6,831,994 B2 | 12/2004 | Bridgham et al. |
| 6,841,128 B2 | 1/2005 | Kambara et al. |
| 7,057,026 B2 | 6/2006 | Barnes et al. |
| 2002/0009744 A1 | 1/2002 | Bogdanov |
| 2002/0025529 A1 | 2/2002 | Quake et al. |
| 2003/0148313 A1 | 8/2003 | Strathmann |
| 2007/0087362 A1 | 4/2007 | Church et al. |

FOREIGN PATENT DOCUMENTS

| | | |
|---|---|---|
| WO | 2005/101045 | 2/2005 |
| WO | 2005/073410 | 8/2005 |
| WO | 2005/082098 | 9/2005 |
| WO | 2006/055521 | 5/2006 |
| WO | 2009/029728 | 3/2009 |

OTHER PUBLICATIONS

PCT/US2008/074678, International Preliminary Report on Patentability mailed Mar. 11, 2010.

Shendure, et al., *Science*, supporting material pp. 1 to 41, vol. 309, 2005, 1728-1732.

Siddiqui, *Nucleic Acids Research*, vol. 34, Publication e83, Jul. 13, 2006, pp. 1-9.

Desselberger, U. et al., "The 3' and 5'-Terminal Sequences of Influenza A, B and C Virus RNA Segments Are Highly Conserved and Show Partial Inverted Complementarity", *Gene*, vol. 8, Feb. 1, 1980, pp. 315-328.

EP13168115.7, European Search Report mailed on Jun. 3, 2015, 4 Pages.

Green, P., "Documentation for PHRAP and Cross_Match", *Version 0.990319*, https://web.archive.org/web/20070612203305/http://www.phrap.org/phredphrap/phrap.html, Jun. 12, 2007, 25 Pages.

Illumina, Inc., "DNA Sequencing with Solexa Technology", Publication No. 770-2007-002, http://www.plantsciences.ucdavis.edu/bit150/2006/JD_Lecture/Lecture%201%20Databses/Solexa_DNAsequencing.pdf, May 1, 2007, 4 Pages.

ALTERNATIVE NUCLEIC ACID SEQUENCING METHODS

CROSS-REFERENCE TO RELATED APPLICATIONS

This application is a continuation of U.S. application Ser. No. 12/200,595 filed Aug. 28, 2008 and claims priority to U.S. application No. 60/968,834 filed Aug. 29, 2007, all of which disclosures are herein incorporated by reference in their entirety.

FIELD

The present disclosure relates to methods and compositions for nucleic acid sequencing.

INTRODUCTION

A large variety of techniques exist for sequencing nucleic acids. However, the various techniques often have problems that can lead to uncertainty in the obtained sequence.

SUMMARY

The present teachings provide, among other things, methods and apparatuses that facilitate more effective sequencing, such as through more accurate nucleic acid sequencing and/or greater read length.

Various embodiments of a method of the present teachings comprise: determining a sequence of a first region of a polynucleotide using a first set of nucleic acid sequencing reagents; and determining a sequence of a second region of the polynucleotide using a second set of nucleic acid sequencing reagents, wherein the first set of nucleic acid sequencing reagents are different from the second set of nucleic acid sequencing reagents.

Various embodiments of a method of the present teachings comprise: applying a first nucleic acid sequencing chemistry to a clonal library derived from a polynucleotide of interest; determining a sequence of a first region of the polynucleotide using a first set of nucleic acid sequencing reagents; and determining a sequence of a second region of the polynucleotide using a second set of nucleic acid sequencing reagents, wherein the first set of nucleic acid sequencing reagents are different than the second set of nucleic acid sequencing reagents.

Various embodiments of a method of the present teachings comprise: determining a sequence of a first region of a polynucleotide of interest using a first nucleic acid sequencing chemistry; and determining a sequence of a second region of the polynucleotide using a second nucleic acid sequencing chemistry. In some embodiments, all or a portion of determining a sequence of a first and second region can be carried out simultaneously.

Various embodiments of a method of the present teachings comprise: determining a sequence of a first region of the polynucleotide using a first set of nucleic acid sequencing reagents, whereby a first nucleic acid sequence is produced; determining a sequence of a second region of the polynucleotide using a second set of nucleic acid sequencing reagents, wherein the first set of nucleic acid sequencing reagents are different than the second set of nucleic acid sequencing reagents, whereby a second nucleic acid sequence is produced, wherein the first region and the second region have at least 1 nucleotide base position in common; and comparing the first nucleic acid sequence and the second nucleic acid. In some embodiments, all or a portion of determining a sequence of a first and second region can be carried out simultaneously.

Various embodiments of a method of the present teachings comprise: fragmenting a polynucleotide for analysis into a plurality of polynucleotide fragments; clonally amplifying at least a part of the polynucleotide fragments, whereby a set of fragment clones is produced; sequencing a first portion of the set of fragment clones, with a first set of nucleic acid sequencing reagents, whereby a first nucleotide base sequence assembly is produced; producing error values for at least some of the bases in the second nucleotide base sequence assembly; sequencing a second portion of the set of fragment clones, with a second set of nucleic acid sequencing reagents, whereby a second nucleotide base sequence assembly is produced; producing error values for at least some of the bases in the second nucleotide base sequence assembly; comparing the first nucleotide base sequence assembly with the second nucleotide base sequence assembly; and selecting at least one base identity between the first and second base sequence assemblies based upon a lower error value for the base identity in the corresponding nucleotide base sequence assembly compared to the base identity of the base in the other base sequence assembly.

In various embodiments, the first region and the second region overlap, while in other embodiments there is no overlap. In some embodiments, the first region and the second region are on different strands of the polynucleotide. In some embodiments, the first region and the second region overlap by at least 5 nucleotides. In some embodiments, the first and second regions overlap by at least 10 nucleotides. In some embodiments, the first region can be adjacent to the second region.

In various embodiments, the polynucleotide is immobilized on a solid support. In some embodiments, the solid support can be a bead or other particles. In various embodiments, the amplified clone is present on an array.

In various embodiments, the polynucleotide can be a single molecule. In some embodiments, the polynucleotide can be an amplified clone. In some embodiments, the amplified clone is produced by PCR. In some embodiments, the PCR is emulsion PCR. In some embodiments, the amplification takes place in a semisolid support. In some embodiments, the amplification takes place on a solid support.

In various embodiments, the first sequencing chemistry or the second sequencing chemistry can be a sequencing by ligation chemistry. In some embodiments, the first sequencing chemistry or the second sequencing chemistry can be a reversible terminator chemistry. In some embodiments, the first sequencing chemistry or the second sequencing chemistry can be a pyrosequencing chemistry. In some embodiments, the first sequencing chemistry and the second sequencing chemistry can be sequencing by ligation chemistry. In some embodiments, the first sequencing chemistry and the second sequencing chemistry are reversible terminator chemistry.

In various embodiments, the clonal library comprises the genome of an organism of interest. In some embodiments, the organism of interest is prokaryotic. In some embodiments, the organism of interest is eukaryotic. In some embodiments, the clonal library comprises clones derived from amplicons derived from a genome of interest. In some embodiments, the clonal library is derived from a nucleic acid library.

Yet further aspects of the present teachings relate to systems for determining a base sequence of polynucleotides.

In various embodiments, the system for determining a base sequence of a polynucleotide of interest comprises an array of polynucleotides for analysis; a flow cell containing the array and having at least one input port; a reservoir set comprising a first set of nucleic acid sequencing reagents, wherein the reservoir set is connection with an input port; a reservoir set comprising a second set of nucleic acid sequencing reagents, wherein the reservoir set is in fluid connection with an input port; a first optical signal collector configured to detect optical signal generated by reactions between the first set of nucleic acid sequencing reagents and the polynucleotides for analysis; and a second optical signal collector configured to detect optical signal generated by reactions between the second set of nucleic acid sequencing reagents and the polynucleotides for analysis. In some embodiments, imaging of reactions from two or more sets of sequencing reagents can be carried out simultaneously.

In various embodiments, the first optical signal collector and the second optical signal collector are the same component. In some embodiments, at least one of the optical signal collectors comprises a CCD. In some embodiments, the system further comprises a laser configured to induce excitation of fluorescent signal present on the array of polynucleotides.

DRAWINGS

Figure 1:
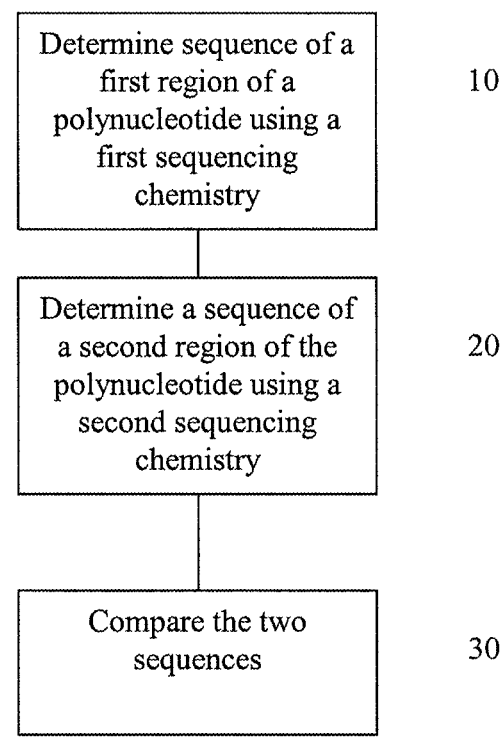
FIG. 1 depicts a flow chart demonstrating one embodiment for analyzing a sequence of a polynucleotide. Two different sequencing chemistries are used to determine a sequence.

The skilled artisan will understand that the drawings are provided for illustration purposes only. The drawings are not intended to limit the scope of the present teachings in any way.

DESCRIPTION OF VARIOUS EMBODIMENTS

For many highly multiplexed parallel sequencing techniques, a large amount of the work occurs in the preparation step of the sample for sequencing, rather than in the sequencing itself. Substantial benefits can be obtained by sequencing polynucleotides via different techniques as described herein. The sequencing reactions can be performed in parallel. In this way, errors that are specific to one technique can be eliminated or reduced with a minimal amount of additional work (as much of the necessary preparation work is carried out regardless of the number of actual sequencing techniques used). Different regions of polynucleotide for analyis may be accessible through different sequencing techniques Generally, the present teachings provide, among other things, methods and apparatuses that facilitate more effective sequencing, such as through more accurate nucleic acid sequencing and/or greater read length. In various embodiments, the present teachings provide methods and apparatus for the highly multiplexed parallel sequencing of nucleic acids.

In various embodiments, a sequence can be analyzed by at least two different sequencing chemistries. This use of multiple sequencing chemistries can increase the accuracy of the sequence of individual clones and the accuracy of a final compiled sequence derived from multiple clones. Different sequencing chemistries tend to produce different errors. Concordance or discordance between the data from the two different chemistries can be taken into account when making a final base call for a given position. Variations in the base and sequence biases of the different chemistries may be also be taken into account when making a final sequence determination. In various embodiments, three or more different sequencing chemistries are employed. In some embodiments, all or part of the sequencing steps using the various chemistries can be carried out simultaneously.

The present teachings further provide, among other things, systems, methods, kits and apparatuses for detecting the sequencing reactions.

SOME DEFINITIONS

Unless otherwise defined, scientific and technical terms used in connection with the invention described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for chemical synthesis, chemical analysis, recombinant nucleic acid, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques of described herein are those well known and commonly used in the art.

As utilized in accordance with the embodiments provided herein, the following terms, unless otherwise indicated, shall be understood to have the following meanings:

The term "nucleic acid sequencing chemistry" as used herein refers to a type of chemistry and associated methods used to sequence a polynucleotide to produce a sequencing result. A wide variety of sequencing chemistries are known in the art. Examples of various types of sequencing chemistries useful in various embodiments disclosed herein include, but are not limited to, Maxam-Gilbert sequencing, chain termination methods, dye-labeled terminator methods, sequencing using reversible terminators, sequencing of nucleic acid by pyrophosphate detection ("pyrophosphate sequencing" or "pyrosequencing") and sequencing by ligation. Such sequencing chemistries and corresponding sequencing reagents are described, for example, in U.S. Pat. Nos. 7,057,026, 5,763,594, 5,808,045, 6,232,465, 5,990,300, 5,872,244, 6,613,523, 6,664,079, 5,302,509, 6,255,475, 6,309836, 6,613,513, 6,841,128, 6,210,891, 6,258,568, 5,750,341, 6,306,597, PCT Publication Nos. WO91/06678A1, WO93/05183A1, WO6074351A2, WO03054142A2, WO03004690A2, WO07002204A2, WO07002204A2, WO06084132A2 and WO06073504A2, which are incorporated by reference in their entireties.

The term "sequencing reagents" as used herein refers to reagents used for sequencing of nucleic acid. Depending on the type of sequencing chemistry, various sequencing reagents can be used. "Sequencing reagents" includes, but are not limited to, appropriate primers, nucleotides, dideoxynucleotides, reverse transcriptase, RNAse, nucleic acid polymerizing agent (e.g. Taq polymerase), RNA polymerizing agents (e.g. Qβ replicase), detectable labels, cleavable linkers, magnesium, ligation agents, cleavage reagents, universal bases, etc. In some embodiments, the four different dideoxynucleotides are labeled with different fluorescent dyes (e.g., for automated nucleic acid sequence analysis). Skilled artisans can select appropriate reagents. Exemplary types of sequencing chemistries are listed above, and several are described in more detail below.

The phrase "different strands of a polynucleotide" as used herein refers to nucleic acid strands which are not from the same strand of a duplex polynucleotide. The different strands may or may not be complementary, or may share an overlapping region of complementarity. The number of overlapping nucleotides can vary from one nucleotide to complete overlap of the entire region. In some embodiments, the different strands of a polynucleotide share an overlapping region of complementarity of at least five nucleotides. In other embodiments, the different strands of a polynucleotide share an overlapping region of complementarity of at least ten nucleotides.

The phrase "first region of a polynucleotide" as used herein refers to a first segment of a polynucleotide for which sequence information is desired. The first region may be of any length or sequence. In some embodiments, the first region of a polynucleotide may comprise a fragment of a larger polynucleotide.

The phrase "second region of the polynucleotide" as used herein refers to a segment of a polynucleotide for which sequence information is desired. The second region of the polynucleotide can be of any length or sequence. The second region of the polynucleotide may or may not overlap with a first region of a polynucleotide. In some embodiments, the first region of a polynucleotide and second region of the polynucleotide overlap by at least five nucleotides. In other embodiments, the first region of a polynucleotide and second region of the polynucleotide overlap by at least ten nucleotides. The first region of a polynucleotide and second region of the polynucleotide may be on different strands, or the same strand, of the polynucleotide. In some embodiments, the second region of a polynucleotide may comprise a fragment of a polynucleotide. In some embodiments, the second region of a polynucleotide is on a different polynucleotide fragment than a first region of the polynucleotide. In some embodiments, the second region of a polynucleotide is on the same polynucleotide fragment as a first region of the polynucleotide. In various embodiments, a third or additional regions are contemplated.

The phrase "first set of nucleic acid sequencing reagents" as used herein refers to a set of reagents used for sequencing to produce a sequencing result that is to be compared to the sequencing result obtained using one or more other sets of nucleic acid sequencing reagents.

The phrase "second set of nucleic acid sequencing reagents" as used herein refers to a set of reagents used for sequencing to produce a sequencing result that is to be compared to the sequencing result of one or more other sets of nucleic acid sequencing reagents. Sequencing reagents may vary depending on the type of sequencing. The second set of nucleic acid sequencing reagents may or may not be the same as the first set of nucleic acid sequencing reagents. In various embodiments, a third or additional sets can be employed.

The phrase "first set of nucleic acid sequencing reagents are different from the second set of nucleic acid" means that either the first or second set of nucleic acid sequencing reagents contains at least one component that is not in the other set. The first and second sets of nucleic acid sequencing reagents can be used to perform different types of sequencing chemistry, but with at least one differing reagent. Alternatively, the first and second sets of nucleic acid sequencing reagents can be used to perform the same type of sequencing chemistry, but with at least one differing reagent.

As used herein, the terms "polynucleotide" and "oligonucleotide" are used interchangeably and mean single-stranded and double-stranded polymers of nucleotide monomers (nucleic acids), including, but not limited to, 2'-deoxyribonucleotides (nucleic acid) and ribonucleotides (RNA) linked by internucleotide phosphodiester bond linkages, e.g. 3'-5' and 2'-5', inverted linkages, e.g. 3'-3' and 5'-5', branched structures, or analog nucleic acids. Polynucleotides have associated counter ions, such as $H^+$, $NH_4^+$, trialkylammonium, $Mg^{2+}$, $Na^+$ and the like. A polynucleotide can be composed entirely of deoxyribonucleotides, entirely of ribonucleotides, or chimeric mixtures thereof. Polynucleotides can be comprised of nucleobase and sugar analogs. Polynucleotides typically range in size from a few monomeric units, e.g. 5-40 when they are more commonly frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine.

As used herein, the term "nucleic acid sequence" or "nucleobase sequence" is any section of a polymer that comprises nucleobase-containing subunits. Non-limiting examples of suitable polymers or polymer segments include oligonucleotides, oligoribonucleotides, peptide nucleic acids and analogs and chimeras thereof.

The term "immobilized" is art-recognized and, when used with respect to a nucleic acid, refers to a condition in which the nucleic acid is attached to a surface with an attractive force stronger than attractive forces that are present in the intended environment of use of the surface, and that act on the species.

The term "organism" is used herein to indicate any living or nonliving entity that comprises nucleic acid that is capable of being replicated and is of interest for sequence determination. It includes, without limitation, plasmids, viruses, prokaryotic, archaebacterial and eukaryotic cells, cell lines, fungi, protozoa, plants, animals, etc.

The phrase "closed complex single molecule sequencing" as used herein refers to a sequencing chemistry based on pyrosequencing involving the natural catalytic cycle of DNA polymerase to capture a single nucleotide on an immobilized primer/template. Closed complex single molecule sequencing chemistry and corresponding sequencing reagents are described, for example, in U.S. Pat. No. 7,264,934.

The phrase "nanoscale fluidic sequencing" as used herein refers to a sequencing chemistry involving nanopores to measure an electric current from individual DNA molecules that will identify individual bases.

Exemplary Embodiments

FIG. 1 depicts a flowchart showing steps that can be used to perform a variety of methods or procedures. In some embodiments, described more fully below, the sequence of a first region of a polynucleotide is determined using a first sequencing chemistry 10. Next, a sequence of a second region of the polynucleotide is determined using a second sequencing chemistry 20. The two sequences are then compared 30. Any differences in the two sequences are thereby identified, thus obtaining a more accurate sequencing result.

Figure 2:
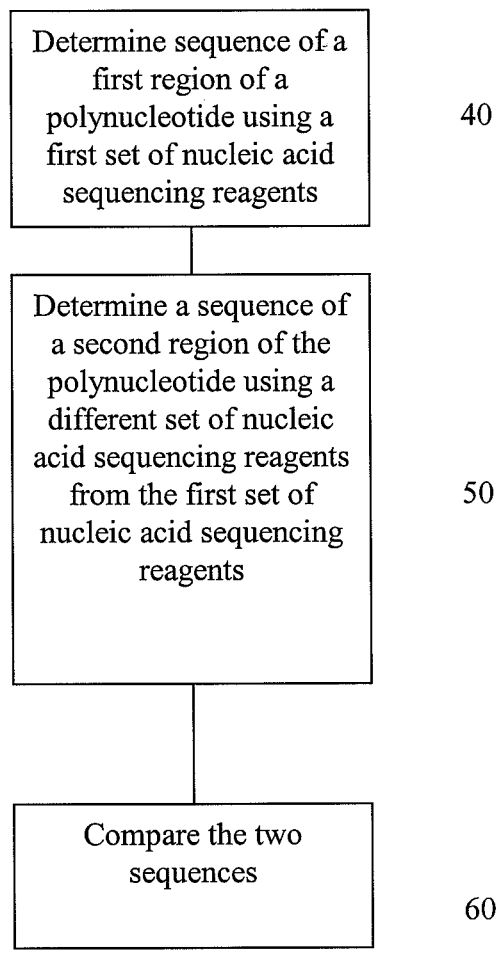
FIG. 2 depicts a flow chart demonstrating another embodiment for analyzing a sequence of a polynucleotide. Two different sets of nucleic acid sequencing reagents are used to determine a sequence.

FIG. 2 depicts a flowchart showing steps that can be used in some embodiments. A first nucleic acid sequence can be determined for a first region of a polynucleotide using a first set of nucleic acid sequencing reagents 40. A second nucleic acid sequence can be determined for second region of the polynucleotide using a second set of nucleic acid sequencing reagents 50. In the illustrated embodiment, the second set of nucleic acid sequencing reagents is different from the first set of nucleic acid sequencing reagents. The first and second region can have at least 1 nucleotide base position in common. The first nucleic acid sequence can then be compared to the second nucleic acid sequence 60. Additional sequences can be determined using additional sets of nucleic acid sequencing reagents and compared to the first and second nucleic acid sequences.

In some embodiments, at least one error value for at least one of the bases in the first or second region of a polynucleotide can be produced using known methods. In some embodiments, error values are calculated according to methods disclosed in, for example, U.S. Patent Application Publication No. 20040053246, filed Oct. 23, 2002, which is incorporated herein by reference in its entirety. The error values may be used as a basis for choosing a base identity where there is a discrepancy when comparing nucleic acid sequences. In some embodiments, the base identity is selected between the first and second nucleic acid sequences based upon a lower error value for the base identity in the corresponding nucleic acid sequence compared to the base identity of the base in the other nucleic acid sequence. In some embodiments, a region that may contain errors based on known issues with a sequencing chemistry is identified. The sequence of this region is compared to a sequence obtained using a sequencing chemistry that does not have the same error issues. For example, where the error rate for sequencing a region (e.g., an area of high GC content) is known to be higher for a first sequencing chemistry versus a second sequencing chemistry, the base identity can be selected from the sequence determined using the second sequencing chemistry.

The sequence of a polynucleotide can be determined using a sequencing chemistry. There are a wide variety of sequencing chemistries known in the art. As discussed above, examples of various types of sequencing chemistries useful in various embodiments disclosed herein include, but are not limited to, Maxam-Gilbert sequencing, chain termination methods, dye terminator methods, sequencing using reversible terminators, sequencing of nucleic acid by pyrophosphate detection ("pyrophosphate sequencing" or "pyrosequencing"), sequencing by ligation, closed complex single molecule sequencing, nanoscale fluidic sequencing, and force spectroscopy platform sequencing. Such sequencing chemistries and corresponding reagents are described, for example, in U.S. Pat. Nos. 7,057,026, 5,763,594, 5,808,045, 6,232,465, 5,990,300, 5,872,244, 6,613,523, 6,664,079, 5,302,509, 6,255,475, 6,309836, 6,613,513, 6,841,128, 6,210,891, 6,258,568, 5,750,341, 6,306,597, PCT Publication Nos. WO91/06678A1, WO93/05183A1, WO6074351A2, WO03054142A2, WO03004690A2, WO07002204A2, WO07002204A2, WO06084132A2 and WO06073504A2, which are incorporated by reference in their entireties.

Various reversible terminators useful for nucleic acid sequencing using reversible terminators are known in the art. Reversible terminator methods use reversible versions of labeled terminators, adding one nucleotide at a time, detecting the label corresponding to that position, then removing the blocking group to allow the polymerization of another nucleotide. Blocking groups of reversible terminators may be present at either the 3' position or the 5' position. Alternatively, the reversible terminators may have removable blocking groups on the nucleotide base or 2' position that serve to prevent extension of polynucleotide after incorporating of the reversible terminator until the blocking group is removed. Examples of sequencing using reversible terminators include, but are not limited to, sequencing using nucleosides and nucleotides that are linked to detectable labels via a cleavable linker group as described in U.S. Pat. Nos. 7,057,026 and 6,664,079; sequencing using protected nucleotides as described in U.S. Pat. Nos. 5,763,594, 5,808,045, 5,990,300, 6,232,465 and 5,872,244; sequencing using reversibly blocked nucleotides as described in PCT Publication Nos. WO 91/06678 and WO 2006/074351; sequencing by a base addition sequencing scheme as disclosed in PCT Publication No. 93/05183; sequencing by incorporation as described in U.S. Pat. No. 6,613,513; sequencing using a hydrocarbyldithiomethyl-modified compound as described in U.S. Pat. No. 6,309,836; sequencing using chain terminators as described in U.S. Pat. No. 6,255,475; and sequencing using fluorescently labeled 3'-blocked nucleotide triphosphates as described in U.S. Pat. No. 5,302,509.

Pyrosequencing is a technique in which a complementary sequence is polymerized using an unknown sequence (the sequence to be determined) as the template. Each time a new nucleotide is polymerized onto the growing complementary strand, a pyrophosphate (PPi) molecule is released. This release of pyrophosphate is then detected. Iterative addition of the four nucleotides (dATP, dCTP, dGTP, dTTP) or of analogs thereof (e.g., α-thio-dATP), accompanied by monitoring of the time and extent of pyrophosphate release, permits identification of the nucleotide that is incorporated into the growing complementary strand. Examples of pyrosequencing include, but are not limited to, sequencing using sulfurylase-luciferase fusion proteins as disclosed in PCT Publication No. WO 03/054142; sequencing using a system as described in U.S. Pat. No. 6,841,128; sequencing using enzymatic detection of release of pyrophosphate as described in U.S. Pat. No. 6,210,891; sequencing using base incorporation by the release of pyrophosphate and simultaneous enzymatic nucleotide degradation as described in U.S. Pat. No. 6,258,568; sequencing using densely packed, independent chemical reactions in parallel in a substantially two-dimensional array as described in PCT Publication No. WO 03/004690; and sequencing using 3'-O-modified deoxynucleoside triphosphates as described in PCT Publication No. WO 2007/002204.

Sequencing by stepwise ligation and cleavage is based on repeated cycles of ligation to and cleavage of probes at the terminus of a target polynucleotide. For example, at each such cycle one or more terminal nucleotides are identified and one or more nucleotides are removed from the end of the target polynucleotide, such that further cycles of ligation and cleavage can take place. At each cycle the target sequence is shortened by one or more nucleotides until the nucleotide sequence of the target polynucleotide is determined. Examples of sequencing by ligation include, but are not limited to, sequencing by cycled oligonucleotide ligation and cleavage as described in PCT Publication No. WO 2006/084132; sequencing by counting fluorescently-labeled particles via flow cytometry as described in PCT Publication No. WO 2005/010145; sequencing based on repeated cycles of duplex extension along a single stranded template as described in U.S. Pat. No. 6,306,597; sequencing by producing a ligation product hybridized to a template nucleic acid as described in U.S. Pat. No. 5,403,708; and sequencing by stepwise ligation and cleavage as described in U.S. Pat. No. 5,552,278.

In various embodiments, a sequence may be analyzed by at least two different sequencing chemistries. In various embodiments, three or more different sequencing chemistries are employed.

In some embodiments, the sequence of a first region of a polynucleotide can be determined using a first sequencing chemistry. In some embodiments the first and second regions are different regions of the same strand or complementary strands and they do not overlap. In some embodiments, the sequence of a second region of a polynucleotide can be determined using a second sequencing chemistry. The first and second sequencing chemistries can be the same or they can be different. The first and second regions can be the same, or they can be different. In other embodiments, a third sequencing chemistry is used to determine the sequence of a third region of a polynucleotide. The third region can be the same as the first and/or second regions, or it can be different. The third sequencing chemistry can be the same as the first and/or second sequencing chemistry, or it can be different. Sequencing a first, second and additional regions can be carried out simultaneously in some embodiments.

In some embodiments, the first sequencing chemistry or the second sequencing chemistry can be a sequencing by ligation chemistry. In some embodiments, the first sequencing chemistry or the second sequencing chemistry can be a reversible terminator chemistry. In some embodiments, the first sequencing chemistry or the second sequencing chemistry can be a pyrosequencing chemistry. In some embodiments, the first sequencing chemistry or the second sequencing chemistry can be a closed complex single molecule sequencing chemistry. In some embodiments, the first sequencing chemistry or the second sequencing chemistry can be a nanoscale fluidic sequencing chemistry. In some embodiments, the first sequencing chemistry or the second sequencing chemistry can be a force spectroscopy platform sequencing chemistry.

In some embodiments, the first sequencing chemistry and the second sequencing chemistry can be sequencing by ligation chemistry. In some embodiments, the first sequencing chemistry and the second sequencing chemistry can be reversible terminator chemistry. In some embodiments, the first sequencing chemistry and the second sequencing chemistry can be pyrosequencing chemistry. In some embodiments, the first sequencing chemistry and the second sequencing chemistry can be closed complex single molecule sequencing chemistry. In some embodiments, the first sequencing chemistry and the second sequencing chemistry can be nanoscale fluidic sequencing chemistry. In some embodiments, the first sequencing chemistry and the second sequencing chemistry can be force spectroscopy platform sequencing chemistry.

In some embodiments, the first sequencing chemistry can be a sequencing by ligation chemistry, and the second sequencing chemistry can be a reversible terminator chemistry. In some embodiments, the first sequencing chemistry can be a reversible terminator chemistry, and the second sequencing chemistry can be a sequencing by ligation chemistry. In some embodiments, the first sequencing chemistry can be a reversible terminator chemistry, and the second sequencing chemistry can be a pyrosequencing chemistry. In some embodiments, the first sequencing chemistry can be a pyrosequencing chemistry, and the second sequencing chemistry can be a reversible terminator chemistry. In some embodiments, the first sequencing chemistry can be a sequencing by ligation chemistry, and the second sequencing chemistry can be a pyrosequencing chemistry. In some embodiments, the first sequencing chemistry can be a pyrosequencing chemistry, and the second sequencing chemistry can be a sequencing by ligation chemistry.

In various embodiments disclosed herein, the sequencing can be carried out in an array format. In some embodiments, polynucleotide fragments on an array may be subjected to a first sequencing chemistry. Subsequently, the polynucleotide fragments on the array can be subjected to a second sequencing chemistry. In other embodiments, the polynucleotide fragments on the array can be subjected to a third or more sequencing chemistries.

A particular type of sequencing chemistry can be performed using a variety of different sets of nucleic acid sequencing reagents. For example, in some embodiments a set of nucleic acid sequencing reagents for pyrosequencing can include apyrase. Another set of nucleic acid sequencing reagents for pyrosequencing may not include apyrase, but may include a dATP analogue capable of acting as a substrate for a polymerase but incapable of acting as a substrate for a PPi-detection enzyme.

Different sets of nucleic acid sequencing reagents for sequencing with reversible terminators can include various different reversible terminators known in the art.

In some embodiments, a set of nucleic acid sequencing reagents can include, for example, appropriate primers, nucleic acid nucleotides, dideoxynucleotides, reverse transcriptase, RNAse, and a nucleic acid polymerizing agent (e.g. Taq polymerase). In other embodiments, a set of nucleic acid sequencing reagents for stepwise ligation and cleavage sequencing can include, for example, an RNA polymerizing agent (e.g. Qβ replicase), detectable labels, cleavable linkers, magnesium, ligation agents, cleavage reagents, and universal bases. In other embodiments, a set of nucleic acid sequencing reagents for sequencing by ligation can include, for example, an appropriate primers, ligase (e.g., T4 DNA ligase), and $AgNO_3$. In other embodiments, a set of nucleic acid sequencing reagents for sequencing by ligation can include, for example, octanucleotide probes with 4-fold degenerate bases and DNA ligase. In other embodiments, a set of nucleic acid sequencing reagents for sequencing by ligation can include, for example, labeled oligonucleotides, such as those described in, for example, U.S. Pat. No. 5,750,341. In other embodiments, a set of nucleic acid sequencing reagents for sequencing by ligation can include, for example, any of the reagents for the SOLiD method as described in PCT Publication No. WO 06/084132. In other embodiments, a set of nucleic acid sequencing reagents for pyrosequencing can include, for example, ATP sulfurylase, apyrase, luciferin and luciferase. In other embodiments, set of nucleic acid sequencing reagents for pyrosequencing can include, for example, a specific primer that hybridizes to a sample nucleic acid such that the target position is directly adjacent to the 3' end of the primer, a polymerase, a detection enzyme means for identifying pyrophosphate release, deoxynucleotides including a dATP analogue capable of acting as a substrate for a polymerase but incapable of acting as a substrate for a PPi-detection enzyme, and optionally, dideoxynucleotides. In other embodiments, a set of nucleic acid sequencing reagents for pyrosequencing can include, for example, template nucleic acid, primers, a modified T7 nucleic acid polymerase or exonuclease deficient Klenow nucleic acid polymerase, deoxynucleoside triphosphates, and apyrase. In other embodiments, a set of nucleic acid sequencing reagents for sequencing using reversible terminators can include, for example, nucleosides and nucleotides that are linked to detectable labels via a cleavable linker group. In other embodiments, a set of nucleic acid sequencing reagents for sequencing using reversible terminators can include, for example, a hydrocarbyldithiomethyl-modified compound.

In some embodiments, the sequence of the first region of a polynucleotide can be determined using a first set of nucleic acid sequencing reagents. In some embodiments, the sequence of the second region of a polynucleotide can be determined using a second set of nucleic acid sequencing reagents. In some embodiments, the first set of nucleic acid sequencing reagents is different from the second set of nucleic acid sequencing reagents. In some embodiments, the first set of nucleic acid sequencing reagents is used to perform the same type of sequencing chemistry as a second set of nucleic acid sequencing reagents. In some embodiments, the first set of nucleic acid sequencing reagents is different from the second set of nucleic acid sequencing reagents; and the first set of nucleic acid sequencing reagents is used to perform the same type of sequencing chemistry as a second set of nucleic acid sequencing reagents. In some embodiments, the first set of nucleic acid sequencing reagents is used to perform a different type of sequencing chemistry than the second set of nucleic acid sequencing reagents.

In some embodiments, the first set of nucleic acid sequencing reagents or the second set of nucleic acid sequencing reagents can be a set of reagents for a sequencing by ligation chemistry. In some embodiments, the first set of nucleic acid sequencing reagents or the second set of nucleic acid sequencing reagents can be a set of reagents for a reversible terminator chemistry. In some embodiments, the first set of nucleic acid sequencing reagents or the second set of nucleic acid sequencing reagents can be a set of reagents for a pyrosequencing chemistry. In some embodiments, the first set of nucleic acid sequencing reagents or the second set of nucleic acid sequencing reagents can be a set of reagents for a closed complex single molecule sequencing chemistry. In some embodiments, the first set of nucleic acid sequencing reagents or the second set of nucleic acid sequencing reagents can be a set of reagents for a nanoscale fluidic sequencing chemistry. In some embodiments, the first set of nucleic acid sequencing reagents or the second set of nucleic acid sequencing reagents can be a set of reagents for a force spectroscopy platform sequencing chemistry.

In some embodiments, the first set of nucleic acid sequencing reagents and the second set of nucleic acid sequencing reagents can be a set of reagents for a sequencing by ligation chemistry. In some embodiments, the first set of nucleic acid sequencing reagents and the second set of nucleic acid sequencing reagents can be a set of reagents for a reversible terminator chemistry. In some embodiments, the first set of nucleic acid sequencing reagents and the second set of nucleic acid sequencing reagents can be a set of reagents for a pyrosequencing chemistry. In some embodiments, the first set of nucleic acid sequencing reagents and the second set of nucleic acid sequencing reagents can be a set of reagents for a closed complex single molecule sequencing chemistry.

In some embodiments, the first set of nucleic acid sequencing reagents can be a set of reagents for a sequencing by ligation chemistry, and the second set of nucleic acid sequencing reagents can be a set of reagents for a reversible terminator chemistry. In some embodiments, the first set of nucleic acid sequencing reagents can be a set of reagents for a reversible terminator chemistry, and the second set of nucleic acid sequencing reagents can be a set of reagents for a sequencing by ligation chemistry. In some embodiments, the first set of nucleic acid sequencing reagents can be a set of reagents for a reversible terminator chemistry, and the second set of nucleic acid sequencing reagents can be a set of reagents for a pyrosequencing chemistry. In some embodiments, the first set of nucleic acid sequencing reagents can be a set of reagents for a pyrosequencing chemistry, and the second set of nucleic acid sequencing reagents can be a set of reagents for a reversible terminator chemistry. In some embodiments, the first set of nucleic acid sequencing reagents can be a set of reagents for a sequencing by ligation chemistry, and the second set of nucleic acid sequencing reagents can be a set of reagents for a pyrosequencing chemistry. In some embodiments, the first set of nucleic acid sequencing reagents can be a set of reagents for a pyrosequencing chemistry, and the second set of nucleic acid sequencing reagents can be a set of reagents for a sequencing by ligation chemistry.

In some embodiments, the first region of a polynucleotide and the second region of the polynucleotide can overlap. The first and second regions of a polynucleotide can overlap by at least about 1, 2, 3, 4, 5, 6, 7, 8, 9, 10, 11, 12, 13, 14, 15, 16, 17, 18, 19, 20, 21, 22, 23, 24, 25, 26, 26, 27, 28, 29, 30 or more nucleotides. The overlapping regions can be on the same strand or may be determined from a complementary strand, wherein different sequencing chemistries are applied to the different strands. Nucleic acid base sequence calls in the overlapping regions can be compared with one another to obtain greater accuracy in the overlapping regions. In some embodiments, the first and second regions of a polynucleotide can overlap completely. In some embodiments, the first and second regions of a polynucleotide do not overlap. In some embodiments, the first and second regions of a polynucleotide can be adjacent to one another. For example, the first region can be bases 1-10, and the second region can be bases 11-20.

In some embodiments, the first region of a polynucleotide and the second region of the polynucleotide can be on different strands of the polynucleotide. In various embodiments, the first region of a polynucleotide and the second region of the polynucleotide can be on different strands of the polynucleotide and be complementary. In other embodiments, the first region of a polynucleotide and the second region of the polynucleotide can be on the same strand of the polynucleotide. In various embodiments, the first region of a polynucleotide and the second region of the polynucleotide can be on the same strand of the polynucleotide and overlap.

In some embodiments, the first and second sequencing chemistries can be used to sequence or resequence the same polynucleotide fragment. In other embodiments, the first and second sequencing chemistries can be used to sequence different regions of the same clone. In some embodiments, the first and second chemistries can be applied to different, non-overlapping regions of the same strand of a polynucleotide, or complementary strands. In other embodiments, the first and second sequencing chemistries can be used to sequence partially overlapping regions of the same clone. For example, the first and second sequencing chemistries can be used to sequence from different direct directions on the same strand. Alternatively, the first and second sequencing chemistries can be used to sequence from different direct directions on a complementary strand. In other embodiments, the first and second sequencing chemistries can be applied sequentially along the same strand to extend read length. For example, a polynucleotide strand can be sequenced first by sequencing by ligation, followed by pyrosequencing to extend the final ligation product. In another embodiment, a polynucleotide strand can be sequenced first by sequencing by ligation, followed by reversible terminator chemistry to extend the final ligation product.

The polynucleotide for sequencing can be prepared in essentially the same manner as a sample for sequence analysis in any number of traditional methods of highly multiplexed parallel sequencing. Such methods result in the clonal amplification of single DNA molecules so as to provide large enough quantities of target DNA for the sequencing chemistry and detection system employed. The clonal amplification products can be on a solid support. In some embodiments, multiple clones may be on a single solid support. In some embodiments, multiple solid supports, each containing an individual clone, may be immobilized on a second solid support so as to maintain separation between the clones. Emulsion PCR on solid supports is described, for example, in PCT Publication No. WO 02/103011A2, PCT Publication No. WO05010145A2 and Diehl, et al. *Nature Methods* Vol. 3, No: 7 pp 551-559 (2006). Clonal amplification to form individual polonies (or colonies) form single molecules are described in, among other places, U.S. Pat. No. 6,001,568. Clonal amplification to form clones on solid supports using PCR can also be found, among other places in, U.S. Pat. Nos. 5,641,658, 6,060,288, 6,090,592, and PCT application WO 07/060456A1. In some embodiments, the polynucleotide to be sequenced can be a single molecule. The polynucleotide can consist of any number of nucleotides. In some embodiments, the polynucleotide can consist of about 1 nucleotide to about 20,000 nucleotides. In some embodiments, the polynucleotide can consist of about 20 nucleotides to about 2,000 nucleotides. In some embodiments, the polynucleotide consists of about 100 to 500 nucleotides.

In various embodiments, the polynucleotide for sequencing may be fragmented. Fragmentation of the polynucleotide may be carried out by any of a number of different methods known in the art. In some embodiments, the polynucleotide may be digested with a nuclease, such as DNAse I. In other embodiments, the nucleic acid may be randomly sheared, for example, by sonication or by passage through a tube having a small orifice. It is also contemplated that the nucleic acid may also be partially digested with one or more restriction enzymes, such that certain points of cross-over may be retained statistically. In some embodiments, the polynucleotide may be fragmented into a plurality of polynucleotide fragments. The polynucleotides to be sequenced can contain one or more universal priming sites or known or predetermined sequence. Universal priming sites can be introduced in a variety of ways, including, for example, ligation, amplification primers, and cloning vectors.

In some embodiments, oligonucleotide adapters can be ligated to one or both ends of the polynucleotide fragments. The oligonucleotide adapters may be useful for amplifying the polynucleotide fragments. For example, the sequence of the ligated adapters may serve as binding sites for polymerase chain reaction (PCR)-based amplification.

In various embodiments, clonally amplifying at least a portion of the polynucleotide fragments produces a set of fragment clones. The polynucleotide can be clonally amplified through techniques such as PCR, for example, such as emulsion PCR and bridge PCR, or polony formation, which are described in, for example, U.S. Pat. Nos. 5,616,478, 5,958,698, 6,001,568, 5,641,658, 6,060,288, 6,090,592, PCT Publication Nos. WO05010145A2, WO05073410A2, WO04069849A2, WO05082098A2, WO 2007/060456, WO9844151A1, and WO0018957A1, which are incorporated by reference in their entireties. In various embodiments, the amplification can be solid phase amplification.

In some embodiments, emulsion PCR can be used to amplify polynucleotides. Methods for forming emulsions are known in the art. For example, emulsions can be formed by mixing an aqueous phase with an oil phase. In some embodiments, amplification can be carried out using a water-in-oil including, for example, numerous droplets of the PCR reaction mixture in a bulk oil phase. In some embodiments, the PCR method can consist of a two-step thermal cycle. The first step can be carried out using the water-in-oil emulsion. During this step, the template DNA can be amplified in the limited volume of the droplets in the water-in-oil emulsion. The water-in-oil emulsion can then be broken and the second PCR step can be carried out.

In various embodiments, bridge PCR can be used to amplify polynucleotides. Bridge PCR is described in, among other places, U.S. Pat. No. 5,641,652 and PCT published application WO/08002502A2. Bridge PCR may be used to effect clonal amplification. Bridge amplification is a technology that uses primers bound to a solid phase for the extension and amplification of solution phase target nucleic acid sequences. During the annealing step, the extension product from one bound primer forms a bridge to the other bound primer. All amplified products are covalently bound to the surface, and can be detected and quantified without electrophoresis. For example, primers carrying 5'-amines can be covalently attached to, for example, silica, polymethylmethacrylate, or polystyrene bead supports and used in place of solution phase primers under standard PCR reaction conditions. Amplification reactions can be monitored by the incorporation of $^{32}$P-labeled deoxynucleotide triphosphates into support-bound form.

In various embodiments, polony formation can be used to amplify polynucleotides. Polony technology is a form of PCR in which the reaction is immobilized in, for example, a thin polyacrylamide gel attached to a microscope slide. As the PCR proceeds, the PCR products diffuse radially within the gel from its immobilized template (e.g., polynucleotides), giving rise to a circular PCR product, or polymerase colony.

In some embodiments, the polynucleotide can be a clone, such as, for example, a gene that is transferred from one organism to another and replicated by genetic engineering techniques. In some embodiments, the clone can be amplified. In some embodiments, the nucleic acid sequencing chemistry can be applied to a clonal library derived from a polynucleotide of interest. The clonal library may comprise the genome of an organism of interest. In some embodiments, the organism of interest is prokaryotic. In other embodiments, the organism of interest is eukaryotic. In some embodiments the clonal library may comprise clones derived from amplicons derived from a genome of interest. In some embodiments the clonal library may be derived from a nucleic acid library.

In some embodiments, the polynucleotide or polynucleotide fragments can be immobilized on a solid support. Single clones of a polynucleotide fragment for analysis can be present on single solid supports, e.g., a single clone on a single bead. In other embodiments, multiples clones can be present and spacially separated from one another on a single solid support. In various embodiments, amplification and/or sequencing of the polynucleotide or fragments can take place on a solid support. A solid support can be any solid phase material upon which a polynucleotide or oligonucleotide can be synthesized, attached or immobilized. A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as, for example, glass, silica, controlled-pore-glass (CPG), or reverse-phase silica. The configuration of a solid support can be in the form of beads, spheres, particles, granules, a gel, a surface, or combinations thereof. Surfaces can be planar, substantially planar, or non-planar. Solid supports can be porous or non-porous, and can have swelling or non-swelling characteristics. A solid support can be configured in the form of a well, depression or other container, vessel, feature or location or position.

Useful solid supports are well known in the art and include those which bind nucleic acids either covalently or non-covalently. Noncovalent supports which are generally understood to involve hydrophobic bonding include naturally occurring and synthetic polymeric materials, such as nitrocellulose, derivatized nylon, and fluorinated polyhydrocarbons, in a variety of forms such as filters or solid sheets. Covalent binding supports are also useful and comprise materials having chemically reactive groups or groups, such as dichlorotriazine, diazobenzyloxymethyl, and the like, which can be activated for binding to polynucleotides.

In various embodiments, amplification of the polynucleotide can take place in a semisolid support. "Semi-solid", as used herein, refers to a compressible matrix with both a solid and a liquid component, wherein the liquid occupies pores, spaces or other interstices between the solid matrix elements. Exemplary semi-solid matrices include matrices made of polyacrylamide, cellulose, polyamide (nylon), and cross-linked agarose, dextran and polyethylene glycol. A semi-solid support may be provided on a second support, e.g., a substantially planar, rigid support, also referred to as a substrate, which supports the semi-solid support.

In some embodiments, the amplified polynucleotides or polynucleotide fragments can be present on an array. In some embodiments, the array may comprise individual molecules rather than clones. As used herein, an array of polynucleotides encompasses an arrangement of polynucleotides present on a solid support or in an arrangement of vessels. An array, as used herein, includes without limitation random arrays, such as, for example, bead arrays. In some embodiments, zipcodes, i.e., sequence tags, can be used to sort on an array. Certain array formats are referred to as a "chip" or "biochip" (M. Schena, Ed. Microarray Biochip Technology, *BioTechnique Books*, Eaton Publishing, Natick, Mass. (2000)). An array can comprise a low-density number of addressable locations, e.g. 1 to about 12, medium-density, e.g. about a hundred or more locations, or a high-density number, e.g. a thousand or more. Typically, the array format can be a geometrically-regular shape that allows for fabrication, handling, placement, stacking, reagent introduction, detection, and storage. The array can be configured in a row and column format, with regular spacing between each location. Alternatively, the locations can be bundled, mixed, or homogeneously blended for equalized treatment and/or sampling. An array can comprise a plurality of addressable locations configured so that each location is spatially addressable for high-throughput handling, robotic delivery, masking, and/or sampling of reagents and/or by detection means including scanning by laser illumination and confocal and/or deflective light gathering. The array may comprise one or more "addressable locations," e.g., "addressable positions," that is, physical locations that comprise a known type of molecule.

One or more types of fiducials may be scattered among the samples to be analyzed to aid in the image analysis or alignment. In various embodiments, the samples further comprise at least one fiducial. By "fiducial" or "marker" or "registration point" herein is meant a physical reference feature or characteristic that allows precise comparisons of sequential data images of an array. The use of fiducials is useful for a variety of reasons. In general, the sequencing methods can involve monitoring of objects, i.e. nucleic acids, located at spatially distinct locations (features) over the course of several data image frames taken over time. Any shifting that occurs from frame to frame complicates the analysis of the agents. By incorporating permanent fiducials into the assay structure, each data image can be aligned, either manually or automatically, to allow accurate comparison of the images, and control for translation (i.e. a shift in an X-Y direction) and/or rotation as well as reduction or enlargement of the image. In addition, when fluorescence based assays are used (either for decoding or analyte assaying or both), in any given image, a particular region or feature may or may not emit fluorescence, depending on the label characteristics and the wavelength being interrogated, or the presence or absence of an analyte or DBL, etc. In some embodiments, image analysis can be carried out simultaneously detectable signal produced by two or more sets of reagents.

Various systems for sequencing polynucleotides on an array are described in, for example, U.S. Pat. Nos. 6,406,848, 6,654,505, 6,806,052 and 6,831,994, which are incorporated by reference in their entireties. Typically, sequencing chemistries generate a detectable signal indicative of the presence of a specific nucleotide base. For example, an optical signal such as a fluorescent, colorimetric, chemiluminescent, radioactive or mass tag (for use, for example, with mass spectrometry) signal may be generated. Therefore, it is desirable to have a system having multiple types of detection systems to detect each type of signal of interest.

A feature of some embodiments of the system for determining a base sequence of a polynucleotide of interest is disclosed in accordance with various embodiments of the present invention. In some embodiments, a system for determining a base sequence of a polynucleotide of interest can comprise a flow cell containing polynucleotides for analysis having at least one input port; a reservoir set comprising a first set of nucleic acid sequencing reagents, wherein the reservoir set is connection with an input port; a reservoir set comprising a second set of nucleic acid sequencing reagents, wherein the reservoir set is in fluid connection with an input port; a first optical signal collector configured to detect optical signal generated by reactions between the first set of nucleic acid sequencing reagents and the polynucleotides for analysis; and a second optical signal collector configured to detect optical signal generated by reactions between the second set of nucleic acid sequencing reagents and the polynucleotides for analysis. In some embodiments, the polynucleotides for analysis are on an array contained in the flow cell. In some embodiments, the first and second optical signal collectors are the same component. In other embodiments they are different. In some embodiments, optical signals generated by the first set of sequencing reagents and optical signals generated by the second set of sequencing reagents are collected simultaneously. The system can readily be expanded for adding additional sets of sequencing reagents.

A key feature of some embodiments of the system is the flow cell. In various embodiments, the body of the flow cell can comprise at least one inlet port and at least one reservoir set. In various embodiments, the flow cell can comprise two reservoir sets. The inlet port and reservoir set can be formed by standard micromachining techniques, e.g. Ekstrom et al., International patent application PCT/SE91/00327; Brown, U.S. Pat. No. 4,911,782; Harrison et al., *Anal. Chem.* 64: 192-1932 (1992); and the like. The flow cell may be constructed from any of several different materials including glass, silicon, polyethylene, polyester, teflon, other plastics, and the like. In various embodiments, key functions of the flow cell include i) holding a population of polynucleotides in a substantially immobilized planar array, or monolayer, during a sequence of processing steps, ii) ensuring that nucleic acid sequencing reagents can access each polynucleotide during each step of a process, and iii) minimizing processing reagent usage. The degree of immobilization required may vary among different embodiments.

In various embodiments, the first optical signal collector and the second optical signal collector are the same component. In various embodiments, one of the optical signal collectors comprises a CCD. In various embodiments, the system further comprises a laser configured to induce excitation of fluorescent signal present on the array of polynucleotides.

In some embodiments of the system, the first optical signal collector or second optical signal collector detects fluorescent signals. In some embodiments of the system, the first optical signal collector and second optical signal collector detects fluorescent signals. In some embodiments of the system, the first optical signal collector or second optical signal collector detects chemiluminescent signals. In other embodiments, the system can have detection systems for detecting both colorimetric signals and chemiluminescent signals. In other embodiments, the system can have detection systems for detecting both fluorescent signals and chemiluminescent signals. In other embodiments, the system can have detection systems for detecting fluorescent, colorimetric signals and chemiluminescent signals.

The first and second sets of nucleic acid sequencing reagents can be the same or different. The first and second sets of nucleic acid sequencing regents can be used to perform the same type of sequencing chemistry or different sequencing chemistries. The first and second sets of nucleic acid sequencing reagents can be used to perform the same type of sequencing chemistry and have a least one reagent different between the sets. In some embodiments of the system, the first set of nucleic acid sequencing reagents or the second set of nucleic acid sequencing reagents can be a set of reagents for a sequencing by ligation chemistry. In some embodiments of the system, the first set of nucleic acid sequencing reagents or the second set of nucleic acid sequencing reagents can be a set of reagents for a reversible terminator chemistry. In some embodiments of the system, the first set of nucleic acid sequencing reagents or the second set of nucleic acid sequencing reagents can be a set of reagents for a pyrosequencing chemistry. In some embodiments of the system, the first set of nucleic acid sequencing reagents or the second set of nucleic acid sequencing reagents can be a set of reagents for a closed complex single molecule sequencing chemistry. In some embodiments of the system, the first set of nucleic acid sequencing reagents or the second set of nucleic acid sequencing reagents can be a set of reagents for a nanoscale fluidic sequencing chemistry. In some embodiments of the system, the first set of nucleic acid sequencing reagents or the second set of nucleic acid sequencing reagents can be a set of reagents for a force spectroscopy platform sequencing chemistry.

In some embodiments of the system, the first set of nucleic acid sequencing reagents and the second set of nucleic acid sequencing reagents can be a set of reagents for a sequencing by ligation chemistry. In some embodiments of the system, the first set of nucleic acid sequencing reagents and the second set of nucleic acid sequencing reagents can be a set of reagents for a reversible terminator chemistry. In some embodiments of the system, the first set of nucleic acid sequencing reagents and the second set of nucleic acid sequencing reagents can be a set of reagents for a pyrosequencing chemistry. In some embodiments of the system, the first set of nucleic acid sequencing reagents and the second set of nucleic acid sequencing reagents can be a set of reagents for a closed complex single molecule sequencing chemistry. In some embodiments of the system, the first set of nucleic acid sequencing reagents and the second set of nucleic acid sequencing reagents can be a set of reagents for a nanoscale fluidic sequencing chemistry. In some embodiments of the system, the first set of nucleic acid sequencing reagents and the second set of nucleic acid sequencing reagents can be a set of reagents for a force spectroscopy platform sequencing chemistry.

In some embodiments of the system, the first set of nucleic acid sequencing reagents can be a set of reagents for a sequencing by ligation chemistry, and the second set of nucleic acid sequencing reagents can be a set of reagents for a reversible terminator chemistry. In some embodiments of the system, the first set of nucleic acid sequencing reagents can be a set of reagents for a reversible terminator chemistry, and the second set of nucleic acid sequencing reagents can be a set of reagents for a sequencing by ligation chemistry. In some embodiments of the system, the first set of nucleic acid sequencing reagents can be a set of reagents for a reversible terminator chemistry, and the second set of nucleic acid sequencing reagents can be a set of reagents for a pyrosequencing chemistry. In some embodiments of the system, the first set of nucleic acid sequencing reagents can be a set of reagents for a pyrosequencing chemistry, and the second set of nucleic acid sequencing reagents can be a set of reagents for a reversible terminator chemistry. In some embodiments of the system, the first set of nucleic acid sequencing reagents can be a set of reagents for a sequencing by ligation chemistry, and the second set of nucleic acid sequencing reagents can be a set of reagents for a pyrosequencing chemistry. In some embodiments of the system, the first set of nucleic acid sequencing reagents can be a set of reagents for a pyrosequencing chemistry, and the second set of nucleic acid sequencing reagents can be a set of reagents for a sequencing by ligation chemistry.

In some embodiments, two or more sequencing techniques can be run simultaneously, in whole or in part. For example, at least a portion of two or more sequencing techniques can be run at the same time. Thus, in some embodiments, one or more steps of two or more sequencing techniques can occur at the same time. The one or more steps may be the same steps, corresponding steps, or may be different steps. In other embodiments, two or more sequencing techniques can be run simultaneously in whole.

In some embodiments, the two or more sequencing techniques or sets of sequencing reagents used at the same, concurrent, or overlapping times. That is, in some embodiments, two or more of the sequencing methods occur during a same time (although they need not start and stop at the same time in all embodiments). In some embodiments, the two techniques occur in a same room. In some embodiments, the two or more sequencing techniques (e.g., use of the sequencing reagents) can occur at separate times and the initial starting material (e.g., amplified product) can be from the same amplified sample. Thus, in some embodiments, after amplifying a sample one can divide the sample for subsequent application on the various sequencing methods.

In some embodiments, kits are provided for the multiple sequencing process. The kits can comprise reagents for amplification of a starting target nucleic acid sequence, a first set of reagents for sequencing a starting target nucleic acid sequence, a second set of reagents for sequencing the starting target nucleic acid sequence (where the two sets are different from one another). In some embodiments, the amplification reagents are not included. In addition, a set of instructions and error identification guides can be included. Such material can be, for example, in print or in digital form.

In some embodiments, sequencing instruments are provided that are able to sequence nucleic acids using two or more sequencing techniques. In some embodiments, the instrument can be used to simultaneously sequence two or more nucleic acids, in part or in whole, using two are more different sequencing techniques. The instrument can include, for example, one or more flow cells including one or more reservoirs and one or more optical signal collectors. In some embodiments, the sequencing instruments can process signals from two more sequencing chemistries. For example, such instruments can include the ability to process signals from two or more different types of sequencing chemistries such as, for example without limitation, Maxam-Gilbert sequencing, chain termination methods, dye terminator methods, sequencing using reversible terminators, sequencing of nucleic acid by pyrophosphate detection, sequencing by ligation, closed complex single molecule sequencing, nanoscale fluidic sequencing, and force spectroscopy platform sequencing.

In some embodiments, instruments are provided that include data processing capability for comparing the results of the multiple sequencing techniques and selecting the optimal sequence (e.g., least error prone) from each identified sequence based upon the likelihood of an error (or error rate) in one sequence technique compared to the other sequencing technique. In some embodiments, an instrument can have both sequencing signal processing capabilities and data processing capabilities for two or more sequencing chemistries. Instruments for processing signals from multiple sequencing chemistries and/or processing data for comparing results can include, for example, means for receiving raw or clean sequencing data, at least one processor, and/or a storage device for storing standard sequencing data. In some embodiments, the instruments include or be connected to a video display or communications link to another instrument, such as, for example, a computer.

In some embodiments, a computer program is included (or can be provided separately) that compares the results of the multiple sequencing techniques and selects the optimal sequence (e.g., least error prone) from each identified sequence based upon the likelihood of an error (or error rate) in one sequence technique compared to the other sequencing technique. In some embodiments, the program selects the most accurate sequence (or removes the least accurate sequence) for each sequence obtained based upon the likelihood of an error for the specific technique used to obtain the sequence and combines the sequences. In this manner, a single complete, highly accurate, sequence can be provided by the program. In some embodiments, the program performs any of the methods described herein. In some embodiments, the computer program can be used in conjunction with an instrument for processing data from multiple sequencing techniques. In other embodiments, the computer program can be implemented using any multipurpose computer including those generally referred to as personal computers and minicomputers.

EXAMPLES

Aspects of the present teachings can be further understood in light of the following examples, which should not be construed as limiting the scope of the present teachings in any way.

Example 1

This example illustrates possible methods for analysis of a polynucleotide sequence by sequencing two regions of the polynucleotide using sequencing by ligation and pyrosequencing.

Figure 3:
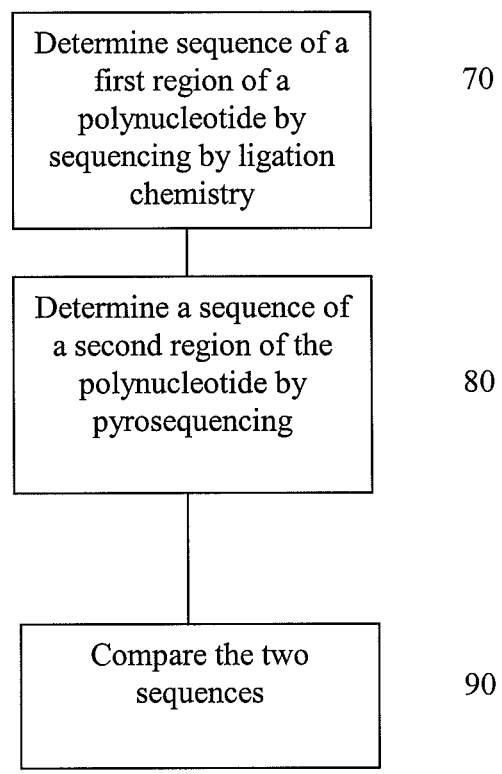
FIG. 3 depicts a flow chart demonstrating another embodiment for analyzing a sequence of a polynucleotide. Sequencing by ligation and pyrosequencing are used to determine a sequence.

The polynucleotide for sequencing is prepared by fragmenting the polynucleotide and clonally amplifying the fragments through emulsion PCR as described below. After amplification, a first region of the polynucleotide is subjected to sequencing using sequencing by ligation, as described below, to determine a first sequence (FIG. 3 at 70). Next, a second region of the polynucleotide is subjected to pyrosequencing, as described below, using to determine a second sequence (FIG. 3 at 80). The first sequence is compared to the second sequence (FIG. 3 at 90). Concordance or discordance between the data from the two different chemistries can be taken into account when making a final base call for a given position. Variations in the base and sequence biases of the different chemistries may be also be taken into account when making a final sequence determination.

Example 2

This example illustrates possible methods for analysis of a polynucleotide sequence by sequencing two regions of the polynucleotide using sequencing by ligation and pyrosequencing.

The polynucleotide for sequencing is prepared by fragmenting the polynucleotide and clonally amplifying the fragments through emulsion PCR as described below. After amplification, a first region of the polynucleotide is subjected to sequencing using sequencing by ligation, as described below, to determine a first sequence. Next, a second region of the polynucleotide is subjected to sequencing using reversible terminators to determine a second sequence. The first sequence is compared to the second sequence. Concordance or discordance between the data from the two different chemistries can be taken into account when making a final base call for a given position. Variations in the base and sequence biases of the different chemistries may be also be taken into account when making a final sequence determination.

Example 3

This example illustrates possible methods for analysis of a polynucleotide sequence by sequencing two regions of the polynucleotide using sequencing by ligation and pyrosequencing.

The polynucleotide for sequencing is prepared by fragmenting the polynucleotide and clonally amplifying the fragments through emulsion PCR as described below. After amplification, a first region of the polynucleotide is subjected to sequencing using reversible terminators to determine a first sequence. Next, a second region of the polynucleotide is subjected to pyrosequencing, as described below, using to determine a second sequence. The first sequence is compared to the second sequence. Concordance or discordance between the data from the two different chemistries can be taken into account when making a final base call for a given position. Variations in the base and sequence biases of the different chemistries may be also be taken into account when making a final sequence determination.

Example 4

This example illustrates possible methods for analysis of a polynucleotide sequence using a first set of nucleotide sequencing reagents and a second set of nucleotide sequencing reagents.

The polynucleotide for sequencing is prepared by fragmenting the polynucleotide and clonally amplifying the fragments through, for example, polony amplification as described below. After amplification, a first region of the polynucleotide is subjected to sequencing using a first set of sequencing reagents to determine a first sequence. The first set of sequencing reagents comprises an RNA polymerizing agent (e.g. Qβ replicase), detectable labels, cleavable linkers, magnesium, ligation agents, cleavage reagents, and universal bases. Next, a second region of the polynucleotide is subjected to sequencing using a second set of sequencing reagents to determine a second sequence. The second set of sequencing reagents comprises primers, a modified T7 nucleic acid polymerase or exonuclease deficient Klenow nucleic acid polymerase, deoxynucleoside triphosphates, and apyrase. The first sequence is compared to the second sequence. Concordance or discordance between the data from the two different chemistries can be taken into account when making a final base call for a given position. Variations in the base and sequence biases of the different chemistries may be also be taken into account when making a final sequence determination.

Example 5

This example illustrates possible methods for analysis of a polynucleotide sequence by determining a sequence of a first region of the polynucleotide with a first sequencing chemistry and determining a sequence of a second region of the polynucleotide with a second sequencing chemistry.

A first region of the polynucleotide is subjected to sequencing using pyrosequencing to determine a first sequence. Next, a second region on a different strand (i.e., the complementary strand) of the polynucleotide that is adjacent to the first region of the polynucleotide is subjected to sequencing using sequencing by ligation to determine a second sequence. The first sequence is compared to the second sequence. Concordance or discordance between the data from the two different chemistries can be taken into account when making a final base call for a given position. Variations in the base and sequence biases of the different chemistries may be also be taken into account when making a final sequence determination.

Example 6

This example illustrates possible methods for the extension of read length by using two different sets of sequencing reagents to read along one strand of a polynucleotide.

In this example, a first region of the polynucleotide is subjected to sequencing using a set of sequencing reagents for sequencing by ligation. Next, a second region of the polynucleotide which is along the same strand as the first region of the polynucleotide is subjected to sequencing using a second set of sequencing reagents that is different from the first set of sequencing reagents, to extend the final ligation product from sequencing of the first region of the polynucleotide.

Example 7

This example illustrates possible methods for analysis of a polynucleotide sequence by sequencing two regions of the polynucleotide that overlap by sequencing with reversible terminators and sequencing by ligation.

A first region of the polynucleotide is subjected to sequencing using pyrosequencing to determine a first sequence. Next, a second region on the same strand of the polynucleotide that overlaps the first region of the polynucleotide by ten nucleotides is subjected to sequencing using sequencing by ligation to determine a second sequence. The first sequence is compared to the second sequence. Concordance or discordance between the data from the two different chemistries can be taken into account when making a final base call for a given position. Variations in the base and sequence biases of the different chemistries may be also be taken into account when making a final sequence determination.

Example 8

This example illustrates possible methods for analysis of a polynucleotide sequence by sequencing the same polynucleotide region using two different sequencing chemistries.

A region of the polynucleotide is subjected to sequencing using pyrosequencing to produce a first nucleic acid sequence. Next, the same region of the polynucleotide is subjected to sequencing by ligation to produce a second nucleic acid sequence. The first sequence is compared to the second sequence. Concordance or discordance between the data from the two different chemistries can be taken into account when making a final base call for a given position. Variations in the base and sequence biases of the different chemistries may be also be taken into account when making a final sequence determination.

Example 9

This example illustrates possible methods for analysis of a polynucleotide sequence by sequencing two regions of the polynucleotide, the two regions being on different strands and overlapping completely.

A first region of the polynucleotide is subjected to sequencing using pyrosequencing to determine a first sequence. Next, a second region on a different strand of the polynucleotide that overlaps completely with the first region of the polynucleotide (i.e., the complement of the first region of the polynucleotide) is subjected to pyrosequencing to determine a second sequence. The first sequence is compared to the second sequence. Concordance or discordance between the data from the two different chemistries can be taken into account when making a final base call for a given position. Variations in the base and sequence biases of the different chemistries may be also be taken into account when making a final sequence determination.

Example 10

This example illustrates possible methods for analysis of a polynucleotide sequence using error values obtained by sequencing using a first set and a second set of nucleic acid sequencing reagents.

In this example, a first portion of a set of fragment clones is sequenced using a first set of nucleic acid sequencing reagents. From this sequencing, a first nucleotide base sequence assembly is produced. Error values for at least some of the bases in a nucleic acid sequence in the first nucleotide base sequence are produced.

Next, a second portion of the set of fragment clones is sequenced with a second set of nucleic acid sequencing reagents. From this sequencing, a second nucleotide base sequence assembly is produced. Error values for at least some of the bases in the second nucleotide base sequence assembly are produced.

Next, the first nucleotide base sequence assembly is compared with the second nucleotide base sequence assembly. At least one base identity is selected between the first and second base sequence assemblies based upon a lower error value for the base identity in the corresponding nucleotide base sequence assembly compared to the base identity of the base in the other base sequence assembly. For example, if the error value of the base identity in the first nucleotide sequence assembly is X, and the error value of the base identity in the second nucleotide sequence is <X, then the identity for the base at that location is selected as the base identity in the second nucleotide sequence.

Example 11

This example illustrates possible methods for amplification of a polynucleotide sequence by emulsion PCR. Other methods and modifications will be apparent to the skilled artisan.

Microemulsions for PCR can be prepared by slight modifications of previously described methods. PCT Publication Nos. WO05010145, WO05073410 and WO04069849; Tawfik, D. S. and Griffiths, A. D. (1998) *Nat Biotech* 16, 652-656; Ghadessy, F. J., Ong, J. L. and Holliger, P. (2001) *Proc Natl Acad Sci* USA 98, 4552-4557, which are incorporated by reference in their entireties. The oil phase can be composed of 4.5% Span 80 (S6760, Sigma, St. Louis, Mo.), 0.40% Tween 80 (Sigma S-8074), and 0.05% Triton X-100 (Sigma T-9284) in mineral oil (Sigma M-3516). The oil phase may be freshly prepared each day. In some embodiments, the aqueous phase can consist of 67 mM Tris-HCl (pH 8.8), 16.6 mM $NH_4SO_4$, 6.7 mM $MgCl_2$, 10 mM (3-mercaptoethanol, 1 mM dATP, 1 mM dCTP, 1 mM dGTP, 1 mM dTTP, 0.05 uM forward primer, 25 uM reverse primer, 45 units Platinum Taq (Invitrogen 10966-034), various amounts of template nucleic acid, and ~108 oligonucleotide-coupled beads in a total volume of 300 ul. In some embodiments the forward primer can be an oligonucleotide whose sequence is identical to the 3' 20-22 nt of the polynucleotide of interest. In some embodiments, a small amount of forward primer is not modified with biotin to maximize the amplification reaction.

In some embodiments, water-in-oil microemulsions can be prepared by drop wise addition of 200 microliters of the aqueous phase to 400 microliters of the oil phase previously placed in a 2 ml round bottom cryogenic vial (430661, Coming, Coming, N.Y.). The drop wise addition may be performed over one minute while the mixture is stirred at 1400 RPM with a magnetic microstir bar (58948-353, VWR, Plainfield, N.J.) on, for example, a VWR model 565 magnetic stirrer. After the addition of the aqueous phase, the mixture is stirred continuously for a total time of about 30 minutes.

Two emulsions can be made at once by placing two tubes in a rack placed at the center of a magnetic stirrer.

The emulsions are aliquotted into wells of a 96 well PCR plate, each containing about 100 ul. In some embodiments, PCR may be carried out under the following cycling conditions: 94° C. for 2 minutes followed by 40 cycles of: 94° C. for 15 seconds, 57° C. for 30 seconds, and 70° C. for 30 seconds. In some embodiments, the PCR products analyzed can range from about 180 to 250 bp.

After PCR cycling, the microemulsion from the wells of the PCR plate may be pooled and broken by the addition 800 microliters of NX buffer (100 mM NaCl containing 1% Triton X-100, 10 mM Tris-HCl, pH 7.5, 1 mM EDTA) in a 1.5 ml tube (Corning 430909). After vortexing for 20 sec, the beads may be pelleted by centrifugation in a microcentrifuge at 8000 rpm (5000 g) for 90 seconds. The top oil phase and all but 300 microliters of the aqueous phase is removed from the tube and 600 microliters of NX buffer can be added. After vortexing for 20 seconds and centrifugation for 90 seconds, the top oil phase and all but-300 microliters of the aqueous phase is removed. The addition of 600 microliters NX buffer, vortexing, and centrifugation is repeated once more and the top oil portion and all but 300 microliters of the aqueous phase is removed. The tube is then placed on a magnet (Dynal MPC-S) and the rest of the supernatant is carefully pipetted off. The beads are washed an additional 3 times with 1×PCR buffer using magnetic separation rather than centrifugation and finally resuspended in 100 microliters of 1×PCR buffer.

Example 12

This example illustrates possible methods for amplification of a polynucleotide by polony amplification. Polony amplification is further described in, for example, U.S. Pat. Nos. 5,616,478, 5,958,698 and 6,001,568; and PCT Publication No. WO05082098A2, which are incorporated by reference in their entireties.

Amplification of a polynucleotide may be carried out in a medium immobilized by using an organic and/or inorganic solid matrix penetrating the medium and having a porous, fibrous, reticulated, coiled, capillary, lamellar or folded texture and which includes the components of a cell-free enzyme system of exponential amplification of nucleic acids. In this medium, the progeny of each molecule (clone) remain in the same zone of the reaction volume where the matrix molecule was initially located. The method permits cloning of nucleic acids in vitro as well as detection of solitary nucleic acid molecules in the sample studied.

All reaction components, including buffer, a thermostable nucleic acid polymerase such as *Thermus aquaticus* nucleic acid polymerase, nucleic acid sample, primers, and substrates are mixed with a degassed acrylamide: N,N'-methylene bisacrylamide solution, and catalysts of acrylamide polymerization [ammonium persulphate and N,N,N',N'-tetrametyl ethylene diamine (TEMED)]. A 0.2-0.4 mm-thick gel layer is then cast between two glass plates, one of which having been treated with a bind silane, and the other with a repel silane. After completion of polymerization, the plate treated with repel silane is removed, the gel is overlaid with a nylon blotting membrane moistened with the reaction buffer, wrapped with a thermostable film, and put onto a thermostating plate with the attached glass plate facing up. To ensure proper heat exchange with the thermostating plate, a thin layer of a mineral oil is placed between the plate surface and the gel-wrapping film. Amplification reaction occurs when temperature of the thermostating plate is cycled (at least 20 cycles are carried out). This is done by employing a temperature-controlling device that is connected through water pipes with the thermostating plate, and that uses three or two water baths with different temperature. Torgensen, H. et al. (1989) *Analyt. Biochem.* 176, 33-35] Weier, H. U. and Gray, J. W. (1988) *nucleic acid* 7, 44-47. Commercially available PCR temperature cyclers can also be used after the heating block is modified to accommodate the gel plate. The reaction components, their concentrations, and conditions of PCR are as described by Saiki et al. (1988) *Science* 239, 487-491.

Example 13

This example illustrates possible methods for amplification of a polynucleotide by solid phase amplification. Solid phase amplification is further described in, for example, U.S. Pat. Nos. 5,641,658, 6,060,288 and 6,090,592; and PCT Publication Nos. WO2007/060456, WO9844151A1 and WO0018957A1, which are incorporated by reference in their entireties.

In this example, a polynucleotide is sonicated to produce a polynucleotide fragment having an approximate length of 1 kb. Adapters containing a target sequence are annealed to at least one end of the polynucleotide fragment. An oligonucleotide is synthesized with a nucleotide sequence complementary to the target sequence of the polynucleotide fragment and the oligonucleotide is immobilized to an epoxy silane derivatized solid support by a 5' amino group. Spacer groups of hexaethylene-glycol are included during synthesis of the oligonucleotide to eliminate steric hindrance during the hybridization reaction. The spacer region is introduced into the synthesized oligonucleotide prior to amino group addition, resulting in a calculated spacer region length of 25 angstroms.

The oligonucleotide can be allowed to hybridize with the target nucleic acid sequence of the polynucleotide fragment in the presence of thermo stable polymerase, enzyme buffer, $^{32}$P labeled and unlabeled dNTP to form a reaction mixture. The reaction mixture is heated to 94° C. for one minute, for denaturation, cooled to 55° C. for one minute, and warmed to 75° C. for 5 minutes to form an amplification product extending from the immobilized oligonucleotide and is complementary to the polynucleotide fragment.

Example 14

This example illustrates possible methods for amplification of a polynucleotide by pyrosequencing.

Pyrosequencing is described in greater detail in, for example, U.S. Pat. Nos. 6,841,128, 6,210,891 and 6,258,568, which are herein incorporated by reference in their entireties.

In this example, an amplified polynucleotide of interest is used as a template for real-time nucleic acid sequencing. The polynucleotide is immobilized onto streptavidin-coated super paramagnetic beads (Dynabeads™ M280-Streptavidin or M450-Streptavidin), and a primer is hybridized to the immobilized template. The immobilized polynucleotides are incubated with either a modified T7 nucleic acid polymerase (Sequenase 2.0; U.S. Biochemical, Cleveland, Ohio, USA), Klenow nucleic acid polymerase (Pharmacia, Biotech, Uppsala, Sweden), or exonuclease deficient (exo-) Klenow nucleic acid polymerase (Amersham, UK). The sequencing procedure is carried out by stepwise elongation of the primer strand upon sequential addition of the different deoxynucleoside triphosphates (Pharmacia, Biotech, Uppsala, Sweden). Washing of the immobilized polynucleotides between each nucleotide addition is performed in two steps: first with a buffer containing 10 mM Tris-HCl (pH 7.5), 0.25 M NaCl, 0.1% Tween 20, and then with 10 mM Tris-acetate (pH 7.5). The PPi released due to nucleotide incorporation is detected by the ELIDA (Nyren, P. (1987) *Anal. Biochem.* 167, 235-238). The luminescence is measured using an LKB 1250 luminometer connected to a potentiometric recorder. The luminometer is calibrated to give a response of 10 mV for the internal light standard. The luminescence output is calibrated by the addition of a known amount of ATP or PPi. The standard assay volume is 0.2 ml and can contain the following components: 0.1 M Tris-acetate (pH 7.75), 2 mM EDTA, 10 mM magnesium acetate, 0.1% bovine serum albumin, 1 mM dithiothreitol, 5 µM adenosine 5'-phosphosulfate (APS), 0.4 mg/ml polyvinylpyrrolidone (360 000), 100 µg/ml D-luciferin (BioOrbit, Finland), 4 µg/ml L-luciferin (BioOrbit, Finland), 0.3 U/ml ATP sulfurylase (ATP:sulfate adenylyl transferase; EC 2.7.7.4) (Sigma Chemical Co., St. Louis, Mo., USA), purified luciferase (Sigma Chemical Co., St. Louis, Mo., USA) in an amount giving a response of 200 mV for 0.1 .mu.M ATP. One pmol of the immobilised nucleic acid-fragment, and 3 pmol nucleic acid polymerase are added to the solution described above. The sequencing reaction is started by adding 40 pmol of one of the nucleotides (Pharmacia, Biotech, Uppsala, Sweden). The reaction can be carried out at room temperature. When the effect of dATP and dATPαS on the luciferase reaction is studied both APS and ATP sulfurylase can be omitted from the assay.

Example 15

This example illustrates possible methods for the determination of a polynucleotide sequence by sequencing by ligation.

In this example, template nucleic acid is prepared by binding the polynucleotide of interest by the 5' end to magnetic beads. Fluorescently labeled primer is premixed with 1× Klenow Buffer. This solution is added to an aliquot of magnetic beads ($10^6$/µL) with attached template after removal of the buffer, and the resulting solution is well mixed under conditions suitable for hybridization. After allowing template/primer hybridization to occur, the primer/buffer is removed, and the beads are washed using a wash buffer, and then resuspended in ligation buffer. The template beads with hybridized labeled primer are then incubated in a mixture containing a first sequencing probe, ligase and buffer under conditions suitable for probe ligation. After ligation of the probe, the beads are washed in a buffer containing sodium acetate. AgNO$_3$ is added to this solution and the resulting mixture is incubated under conditions to allow cleavage. AgNO$_3$ is removed, and the beads were washed once in sodium acetate. The beads are then washed in a neutral buffer, and an aliquot is removed and saved for analysis. The buffer is removed, and the beads are then resuspended in H$_2$O$_5$ and incubated at conditions suitable for ligation with a mixture containing a second sequencing probe, ligase and buffer. After ligation of the second sequencing probe, the beads are washed in a buffer containing sodium acetate. AgNO$_3$ is added to this solution and the resulting mixture is incubated under conditions to allow cleavage. AgNO$_3$ is removed, and the beads were washed once in sodium acetate. The beads are then washed in a neutral buffer, and an aliquot is removed and saved for analysis.

The first and second sequencing probes are synthesized to contain an internal phosphorothiolated thymidine base (sT). The first cleavable probe is ligated to the extendable terminus of the primer using T4 nucleic acid ligase and is then cleaved using silver nitrate. Cleavage removes the terminal 5 nucleotides of the extension probe and generated an extendable terminus on the portion of the probe that remained ligated to the primer. The second cleavable probe is then ligated to the extendable terminus and is then similarly cleaved.

A fluorescent capillary electrophoresis gel shift assay can be used to monitor steps of ligation and cleavage. In this assay, the primer is hybridized to a template strand such that the 5' phosphate can serve as a ligation substrate for incoming oligonucleotide probes (the fluorophore serves as a reporter for mobility-based capillary gel electrophoresis). After each step an aliquot of beads is removed for analysis. Following ligation of oligonucleotide probes, the magnetic beads are collected using a magnet, and the ligated species consisting of the primer and probe(s) ligated thereto is released from the template beads by heat denaturation and subjected to fluorescent capillary electrophoresis using an automated nucleic acid sequencing instrument with labeled size standards. In a typical gel shift, the potential peaks include, i) primer peaks (due to no extension or the lack of primer extension), ii) adenylation peaks (due to the attachment of an adenosine residue at the 5' end of a nonproductive ligation junction by the action of nucleic acid ligase—see Lehman, I. R., *Science*, 186:790-797, 1974), and iii) completion peaks (due to the attachment of an oligo probe).

While it is desirable that the ligation proceed to completion it is not a requirement. For example, it is possible to effectively "cap" any unligated 5' ends by treating with a 5'-phosphatase after the ligation step as described above. In that case, however, there would be a limit to the number of sequential ligations that could be performed, due to attrition of ligatable molecules. With a given number of sequential ligations, the read length will depend on the length of the probe remaining after each ligation/cleavage cycle and on the number of sequencing reactions, each followed by removal of the primer and hybridization of a primer that binds to a different portion of the primer binding site, that can be performed on a given template, also referred to as the number of "resets"). This argues for the use of longer probes with the cleavable linkage located towards the 5' end of the probe. In our experiments, hexamer probes lead to greater amounts of un-ligatable adenylation products than octamers and longer probes. Thus octamers and longer probes will ligate substantially to completion (see below). In addition, adding a fluorescent moiety to the 5' end of a hexamer probe seems to reduce the efficiency of ligation, whereas adding a fluorescent moiety to an octamer probe has little or no effect. For these reasons, use of octamers or longer probes is considered preferable in certain embodiments.

Example 16

This example illustrates possible methods for analysis of a polynucleotide sequence by sequencing two regions of the polynucleotide using sequencing by ligation and pyrosequencing.

The polynucleotide for sequencing is prepared by fragmenting the polynucleotide and clonally amplifying the fragments through emulsion PCR as described below. After amplification, a first region of the polynucleotide is subjected to sequencing using sequencing by ligation, as described below, to determine a first sequence. A second region of the polynucleotide is subjected to pyrosequencing, as described below, using to determine a second sequence. At least a portion of the first and second regions can be sequenced simultaneously. The first sequence is compared to the second sequence. Concordance or discordance between the data from the two different chemistries can be taken into account when making a final base call for a given position. Variations in the base and sequence biases of the different chemistries may be also be taken into account when making a final sequence determination.

It is to be understood that both the foregoing general description and the detailed description are exemplary and explanatory only and are not restrictive of the invention, as claimed. In this application, the use of the singular includes the plural unless specifically stated otherwise. In this application, the word "a" or "an" means "at least one" unless specifically stated otherwise. In this application, the use of "or" means "and/or" unless stated otherwise. Furthermore, the use of the term "including," as well as other forms, such as "includes" and "included," is not limiting. Also, terms such as "element" or "component" encompass both elements or components comprising one unit and elements or components that comprise more than one unit unless specifically stated otherwise.

The section headings used herein are for organizational purposes only and are not to be construed as limiting the described subject matter in any way.

It will be appreciated that there can be an implied "about" prior to the temperatures, concentrations, times, etc. discussed in the present teachings, such that slight and insubstantial deviations are within the scope of the present teachings herein. For example, "a primer" means that more than one primer can, but need not, be present; for example but without limitation, one or more copies of a particular primer species, as well as one or more versions of a particular primer type, for example but not limited to, a multiplicity of different forward primers. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the invention.

INCORPORATION BY REFERENCE

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application; including but not limited to defined terms, term usage, described techniques, or the like, this application controls.

EQUIVALENTS

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A method for sequencing a polynucleotide in a preparation by a sequencing instrument, wherein the sequencing instrument comprises a processor, said method comprising:

obtaining a polynucleotide preparation comprising the polynucleotide, comprising amplifying the polynucleotide in a semisolid support, determining, by the sequencing instrument, a first apparent sequence of a first region of a polynucleotide by subjecting a sample of the polynucleotide preparation to a first type of sequencing technique;

simultaneously determining, by the sequencing instrument, a second apparent sequence of a second region of the polynucleotide that overlaps with the first region, by subjecting a sample of the same polynucleotide preparation to a second different type of sequencing technique, wherein the first and second sequencing techniques are selected from the group consisting of Maxam-Gilbert sequencing, chain termination methods, dye termination methods, sequencing using reversible terminators, sequencing of nucleic acid by pyrophosphate detection, sequencing by ligation, closed complex single molecule sequencing, nanoscale fluidic sequencing, and force spectroscopy platform sequencing;

identifying, by the processor, any discrepancies between the first apparent sequence and the second apparent sequence; and selecting, by the processor, the least error prone sequence from the first apparent sequence and the second apparent sequence based upon the likelihood of an error or error rate in one sequencing technique compared to the other sequencing technique.

2. The method of claim 1, wherein the polynucleotide is immobilized on a solid support.

3. The method of claim 2, wherein the solid support is a bead.

4. The method of claim 1, wherein the polynucleotide is a single molecule.

5. The method of claim 1, wherein the polynucleotide is an amplified clone.

6. The method of claim 5, wherein the amplified clone is produced by PCR.

7. The method of claim 6, wherein the PCR is emulsion PCR.

8. The method of claim 5, wherein the amplification takes place on a solid support.

9. The method of claim 5, wherein the amplified clone is present on an array.

* * * * *